United States Patent
Shverdin et al.

(10) Patent No.: US 12,216,053 B1
(45) Date of Patent: Feb. 4, 2025

(54) SYSTEM AND METHODS FOR DETECTING PATHOGENS USING MULTI-WAVELENGTH SENSING

(71) Applicant: Amazon Technologies, Inc., Seattle, WA (US)

(72) Inventors: Miro Yakov Shverdin, Mountain View, CA (US); Annapurna Karicherla, Cupertino, CA (US); Carla Alejandra Gimenez, Buenos Aires (AR)

(73) Assignee: Amazon Technologies, Inc., Seattle, WA (US)

( * ) Notice: Subject to any disclaimer, the term of this patent is extended or adjusted under 35 U.S.C. 154(b) by 860 days.

(21) Appl. No.: 17/354,710

(22) Filed: Jun. 22, 2021

(51) Int. Cl.
   G01N 1/00       (2006.01)
   C12Q 1/70       (2006.01)
   G01N 21/64      (2006.01)

(52) U.S. Cl.
   CPC .......... *G01N 21/6428* (2013.01); *C12Q 1/70* (2013.01); *G01N 2021/6439* (2013.01)

(58) Field of Classification Search
   None
   See application file for complete search history.

(56) References Cited

U.S. PATENT DOCUMENTS

| | | |
|---|---|---|
| 5,589,351 A | 12/1996 | Harootunian |
| 5,961,451 A | 10/1999 | Reber et al. |
| 9,040,288 B2 | 5/2015 | Handique et al. |
| 2003/0142291 A1 | 7/2003 | Padmanabhan et al. |
| 2009/0253181 A1 | 10/2009 | Vangbo et al. |
| 2011/0201099 A1 | 8/2011 | Anderson et al. |
| 2011/0312841 A1 | 12/2011 | Silverbrook et al. |

(Continued)

FOREIGN PATENT DOCUMENTS

WO   2017132172 A1   8/2017

OTHER PUBLICATIONS

Priye et al., "A smartphone-based diagnostic platform for rapid detection of Zika, chikungunya, and dengue viruses", Scientific Reports, vol. 7, No. 44778, Mar. 20, 2017, 11 pages.

(Continued)

*Primary Examiner* — Jyoti Nagpaul
(74) *Attorney, Agent, or Firm* — Kilpatrick Townsend & Stockton LLP

(57) ABSTRACT

Systems and methods for testing a biological sample for each of two or more target pathogens employ fluorescence detection from a single fluorescence reading chamber. A method of testing a biological sample for each of two or more target pathogens includes forming a detection cycle liquid by combining detection cycle compounds with a biological sample liquid formed from a biological sample. The detection cycle compounds include respective CRISPR enzymes for each of the two or more target pathogens. The respective CRISPR enzymes are tagged with respective spectrally unique fluorescent probes. The detection cycle liquid is exposed to a multi-wavelength fluorescence excitation light. A multi-wavelength fluorescence light emission detection signal indicative of intensity of fluorescence light emitted by the detection cycle liquid over multiple wavelengths is processed to generate detection data indicative of presence or absence of each of the two or more target pathogens in the biological sample.

20 Claims, 7 Drawing Sheets

(56) References Cited

U.S. PATENT DOCUMENTS

| | | |
|---|---|---|
| 2014/0194305 A1 | 7/2014 | Kayyem et al. |
| 2017/0241949 A1 | 8/2017 | Bort et al. |
| 2019/0323001 A1* | 10/2019 | Federowicz ............ C12N 9/22 |
| 2020/0033579 A1 | 1/2020 | Chou et al. |
| 2020/0260066 A1 | 8/2020 | Liu |
| 2021/0362155 A1 | 11/2021 | Williams et al. |

OTHER PUBLICATIONS

U.S. Appl. No. 17/210,832, filed Mar. 24, 2021, Titled: Virus Detection System and Cartridge.

U.S. Appl. No. 17/224,774, filed Apr. 7, 2021, Titled: Systems, Devices, and Methods for Virus Detection via Fluorescence Emission.

* cited by examiner

SYSTEM AND METHODS FOR DETECTING PATHOGENS USING MULTI-WAVELENGTH SENSING

BACKGROUND

Timely and accurate detection of a pathogen (e.g., pathogen, bacteria, fungus, parasite, or other microorganism that can cause disease) is important to effective treatment of a person infected with the pathogen. Timely and accurate detection of the pathogen can also help to inhibit spreading of the pathogen from the infected person via suitable precautions taken based on knowing that the person is infected with the pathogen. Timely and accurate detection of a pathogen is especially important where the pathogen has a high lethality in at least some vulnerable populations (e.g., elderly, diabetic, immune compromised), such as with the SARS-CoV-2 virus.

BRIEF DESCRIPTION OF THE DRAWINGS

Various embodiments in accordance with the present disclosure will be described with reference to the drawings, in which.

DETAILED DESCRIPTION

Figure 1:
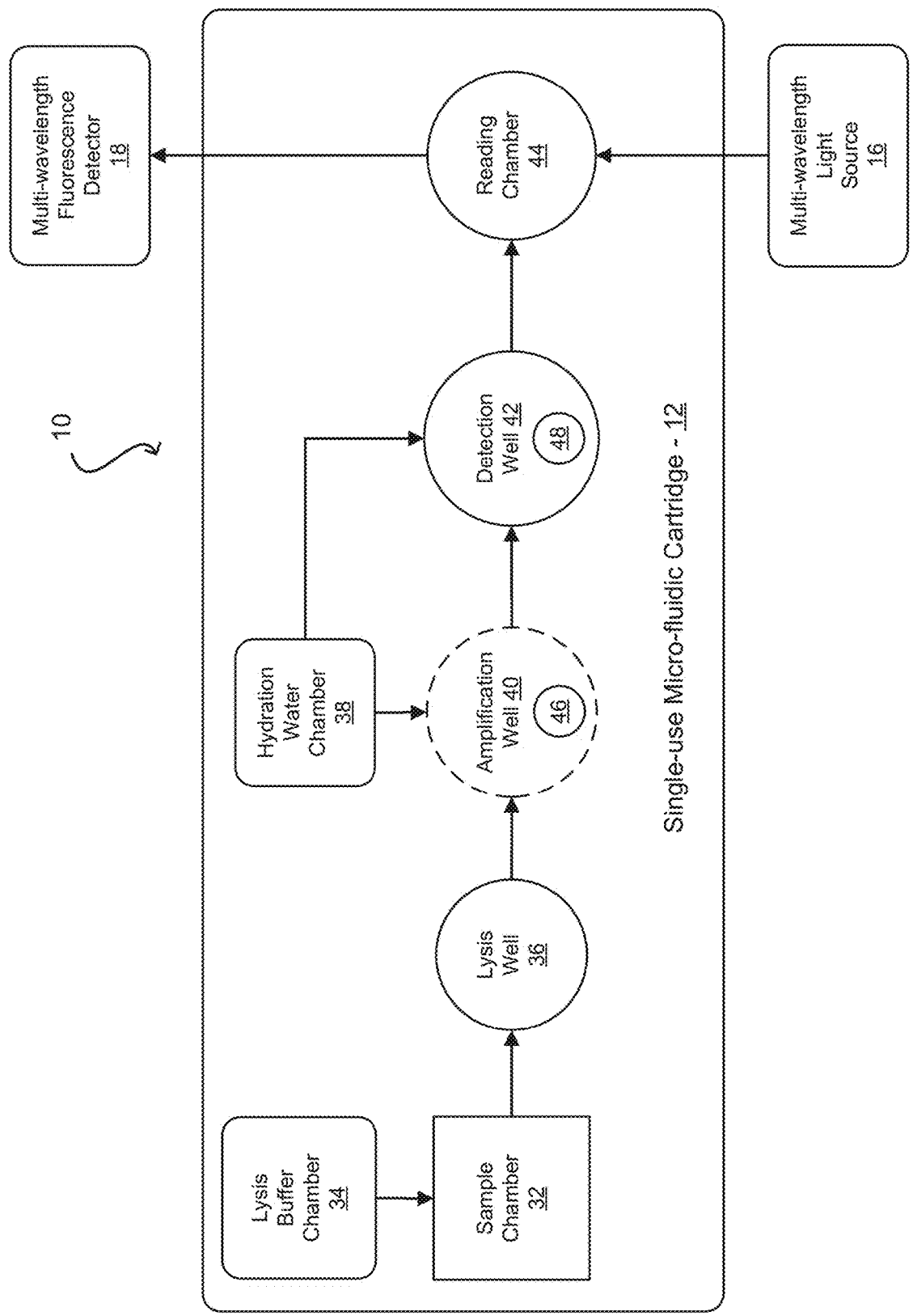
FIG. 1 is a simplified schematic diagram of an approach for testing a biological sample for each of two or more target pathogens using multi-wavelength sensing, in accordance with embodiments.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Systems and methods for testing a biological sample for each of two or more target pathogens employ fluorescence detection from a single fluorescence reading chamber using a multi-wavelength excitation light (e.g., broadband light) and a spectral sensor. In many embodiments, spectrally unique loop-mediated isothermal amplification (LAMP) primers are used for reverse transcription loop-mediated isothermal amplification (RT-LAMP) of each of the two or more target pathogens, followed by Clustered Regularly Interspaced Short Palindromic Repeats (CRISPR) readout. While testing a biological sample for each of two or more target pathogens using of RT-LAMP and CRISP readout is described herein, any other suitable fluorescence detection technique, with or without any suitable amplification technique, can be employed. In many embodiments, two or more different LAMP primers are used, with each of the different LAMP primers used being suitable for a respective one of the two or more target pathogens (e.g., COVID, respiratory pathogens (RP), influenza, etc.). In many embodiments, two or more different readout CRISPR enzymes are used, with each of the different readout CRISPR enzymes being tagged with a spectrally specific fluorescent probe that is specific to a respective one of the two or more target pathogens (e.g., COVID, respiratory pathogens (RP), influenza, etc.). As described herein, fluorescent probes are available in different excitation and emission wavelengths. Fluorescent probes are available as organic dyes or as engineered materials, such as quantum dots. In many embodiments, the presence or absence of each of the two or more target pathogens is determined from a fluorescence light emission detection signal generated by the spectral sensor in response to a fluorescent light emitted by a resulting detection cycle liquid in the single fluorescence reading chamber. By testing a biological sample for each of two or more target pathogens using fluorescence detection from a single fluorescence reading chamber using a multi-wavelength excitation light (e.g., broadband light) and a spectral sensor, the total number of independent channels in a single-use microfluidic cartridge used for point-of-care testing can be reduced as compared to existing approaches that employ a respective fluorescence reading channel for each target pathogen.

In many embodiments, an analysis device is used in conjunction with a single-use cartridge to test a biological sample for each of two or more target pathogens. The system can be adapted for detecting any suitable two or more pathogens including, but not limited to, any suitable combination of two or more of SARS-COV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V. The systems and methods described herein can be used at the point of care, including in very low complexity medical environments. The system and methods described herein can also be used in any other suitable location, such as in a house.

The systems and methods described herein can be used to test for the presence of the two or more target pathogens in a biological sample taken with a swab, nasal or nasopharyngeal. In many embodiments, an analysis device delivers a result in real-time, transmitted to a mobile device application, through a suitable communication connection (e.g., USB cable, WiFi, Bluetooth, etc.).

Turning now to the drawing figures, in which similar reference identifiers refer to similar elements, FIG. 1 is a simplified schematic diagram of an approach 10 for testing a biological sample for each of two or more target pathogens using multi-wavelength sensing, in accordance with embodiments. In the illustrated embodiment, the approach 10 is implemented using a single-use microfluidic cartridge 12 and an analysis device 14 (shown in FIG. 6). The cartridge 12 is configured to receive a portion of a swab on which a biological sample is disposed and operable, via the analysis device 14, to process the biological sample to test whether the biological sample contains any of two or more target pathogens. The analysis device 14 is configured to receive and operatively couple with the cartridge 12 to interact with and operate the cartridge 12. The analysis device 14 includes a multi-wavelength light source 16, a multi-wavelength fluorescence detector 18, a fluid displacement assembly 20, a lysis well heater 22, an amplification well heater 24, a detection well heater 26, a device controller 28, and a communication unit 30.

The cartridge 12 is configured to process the biological sample. The cartridge 12 includes a sample chamber 32, a lysis buffer chamber 34, a lysis well 36, a hydration water chamber 38, an amplification well 40, a detection well 42, and a reading chamber 44. The sample chamber 32 is configured to receive a portion of a swab on which a biological sample is disposed. A lysis buffer solution is stored in the lysis buffer chamber 34. The lysis buffer solution is applied to the swab subsequent to insertion of the swab into the cartridge 12. The device controller 28 controls operation of the fluid displacement assembly 20 to transfer of lysis buffer solution and biological sample from the sample chamber 32 to the lysis well 36. The device controller 28 controls operation of the lysis well heater 22 to heat the lysis buffer solution and the biological sample in the lysis well 36 to enhance lysis of the biological sample. Hydration water is stored in the hydration water chamber 38. The device controller 28 controls operation of the fluid displacement assembly 20 to transfer of liquid from the lysis well 36 and hydration water from the hydration water chamber 38 to the amplification well 40, which contains amplification compounds 46 for each of the two or more target pathogens. In many embodiments, the amplification compounds 46 include loop-mediated isothermal amplification (LAMP) primers that are used for reverse transcription loop-mediated isothermal amplification (RT-LAMP) of each of the two or more target pathogens. In many embodiments, the amplification compounds 46 are formed as a lyophilized bead. The device controller 28 controls operation of the amplification well heater 24 to heat the resulting liquid in the amplification well 40 to produce RT-LAMP of each of the two or more target pathogens (if present in the biological sample). In some embodiments, the cartridge 12 does not include the amplification well 40 so that RT-LAMP is not accomplished. The device controller 28 controls operation of the fluid displacement assembly 20 to transfer liquid from the amplification well 40 to the detection well 42. In many embodiments, the detection well 42 includes detection cycle compounds 48 for each of the two or more target pathogens. In many embodiments, the detection cycle compounds 48 include Clustered Regularly Interspaced Short Palindromic Repeats (CRISPR) enzymes tagged with spectrally distinct fluorescent probes. In many embodiments, two or more different readout CRISPR enzymes are used, with each of the different readout CRISPR enzymes being tagged with a spectrally distinct specific fluorescent probe that is specific to a respective one of the two or more target pathogens (e.g., COVID, respiratory pathogens (RP), influenza, etc.). In many embodiments, the detection cycle compounds 48 are formed as a lyophilized bead. The device controller 28 controls operation of the detection well heater 26 to control the temperature of the resulting liquid in the detection well 42. The device controller 28 controls operation of the fluid displacement assembly 20 to transfer liquid from the detection well 42 to the reading chamber 44.

The device controller 28 controls operation of the multi-wavelength fluorescence light source 16 to emit multi-wavelength excitation light (e.g., white light generated by a broadband light source, multi-wavelength light generated by two or more monochromatic light sources such as light emitting diodes (LEDs)), including wavelengths suitable for exciting the specific fluorescent probes used, onto the liquid in the reading chamber 44. Where at least one of the two or more target pathogens are present in the biological sample, the multi-wavelength excitation light causes the liquid in the reading chamber 44 to emit fluorescent light corresponding to the spectrally distinct fluorescent probes employed and which of the two or more target pathogens that is/are present in the biological sample. The multi-wavelength fluorescence detector 18 generates one or more fluorescence light detection signals in response to the fluorescent light emitted by the liquid in the reading chamber 44. The multi-wavelength fluorescence detector 18 can have any suitable configuration. For example, the multi-wavelength fluorescence detector 18 can include a spectral sensor that generates an output signal indicative of intensity of the fluorescent light emitted over a suitable range of wavelengths (e.g. 350 nm to 1000 nm). Any suitable spectral sensor can be used, such as a chip-scale spectrally resolving sensor (e.g. AMS AS7341). As another example, the multi-wavelength fluorescence detector 18 can include any suitable plurality of individual sensors that are each configured to detect a respective wavelength of fluorescent light emission and generate a signal indicative of intensity of the emitted light having the respective wavelength.

Figure 2:
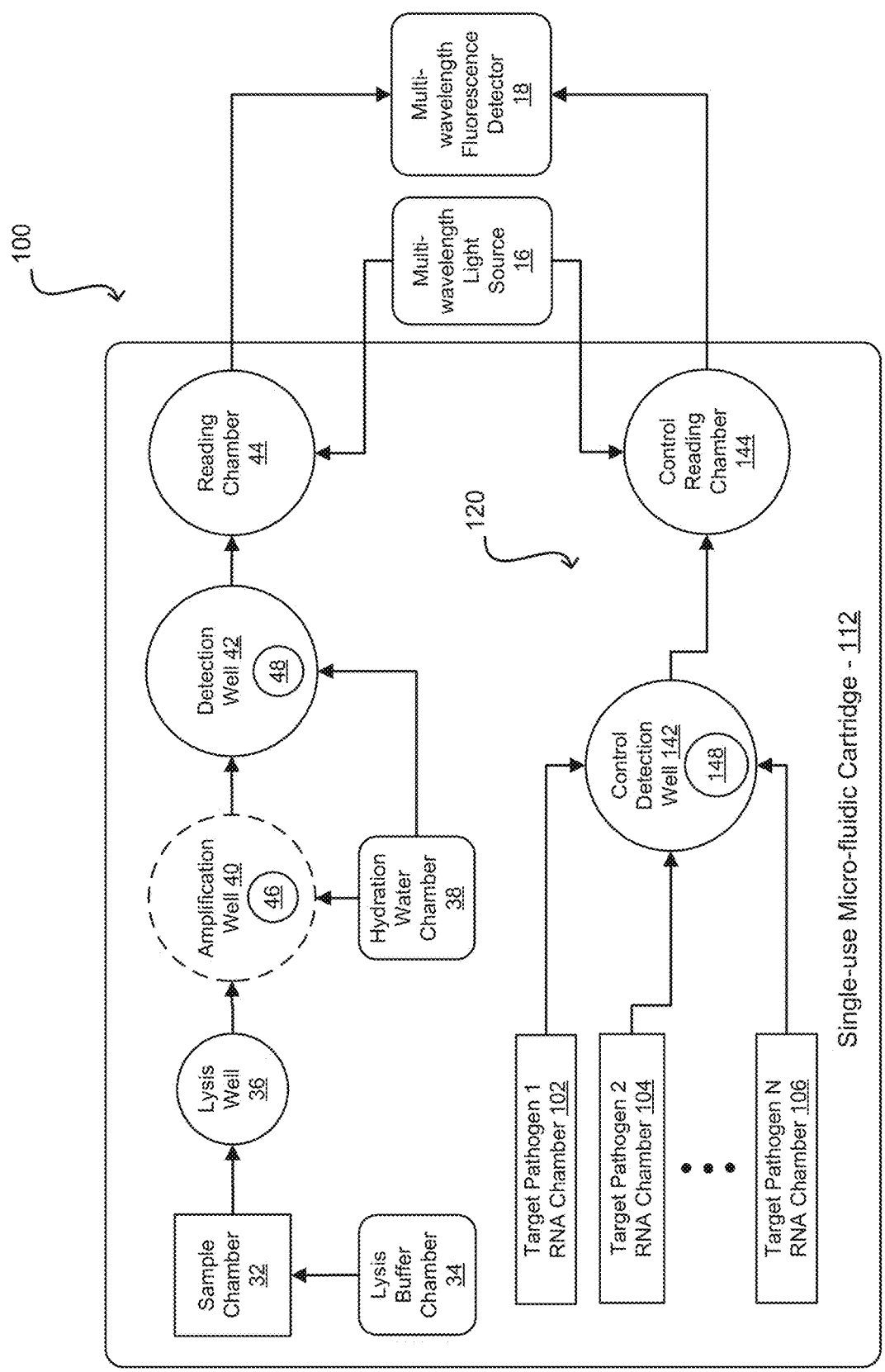
FIG. 2 is a simplified schematic diagram of another approach for testing a biological sample for each of two or more target pathogens using multi-wavelength sensing, in accordance with embodiments.

FIG. 2 is a simplified schematic diagram of an approach 100 for testing a biological sample for each of two or more target pathogens using multi-wavelength sensing, in accordance with embodiments. In the illustrated embodiment, the approach 100 is implemented using a single-use microfluidic cartridge 112 and an analysis device 14 (shown in FIG. 6). The cartridge 112 is configured similar to the cartridge 12, but further includes a control channel 120 that processes combined control samples of ribonucleic acid (RNA) of each of the target pathogens for the generation of a control fluorescent light emission detection signal indicative of whether the cartridge 112 is in a condition to produce a valid detection of the presence or absence of each of the target pathogens.

The control channel 120 includes an RNA chamber 102, 104, 106 for each of the target pathogens, a control detection well 142, and a control reading chamber 144. Each of the RNA chambers 102, 104, 106 contains a respective control sample liquid that includes RNA for a respective one of the target pathogens. The device controller 28 controls operation of the fluid displacement assembly 20 to transfer the control sample liquid from each of the RNA chambers 102, 104, 106 to the control detection well 142. In many embodiments, the control detection well 142 includes control detection cycle compounds 148 for the RNA for each of the two or more target pathogens. In many embodiments, the detection cycle compounds 148 include Clustered Regularly Interspaced Short Palindromic Repeats (CRISPR) enzymes tagged with spectrally distinct fluorescent probes. In many embodiments, two or more different readout CRISPR enzymes are used, with each of the different readout CRISPR enzymes being tagged with a spectrally distinct specific fluorescent probe that is specific to a respective one of the two or more target pathogens (e.g., COVID, respiratory pathogens (RP), influenza, etc.). In many embodiments, the control detection cycle compounds 148 are formed as a lyophilized bead. The device controller 28 controls operation of the detection well heater 26 to control the temperature of the resulting liquid in the control detection well 142. The device controller 28 controls operation of the fluid displacement assembly 20 to transfer liquid from the control detection well 142 to the control reading chamber 144.

The device controller 28 controls operation of the multi-wavelength fluorescence light source(s) 16 to emit multi-wavelength excitation light (e.g., white light generated by a broadband light source, multi-wavelength light generated by two or more monochromatic light sources such as light emitting diodes (LEDs)), including wavelengths suitable for exciting the specific fluorescent probes used, onto the liquid in the control reading chamber 144. Where the cartridge 112 is in a condition to produce a valid detection of the presence or absence of each of the target pathogens, the multi-wavelength excitation light causes the liquid in the control reading chamber 44 to emit fluorescent light corresponding to all of the spectrally distinct fluorescent probes employed. The multi-wavelength fluorescence detector 18 generates one or more fluorescent light detection signals in response to the fluorescent light emitted by the liquid in the control reading chamber 44. In many embodiments, the one or more fluorescent light detection signals is/are processed to determine whether the one or more fluorescent light detection signals match or substantially correspond to pre-established intensity ranges indicative of the presence of each of the target pathogens.

Figure 3:
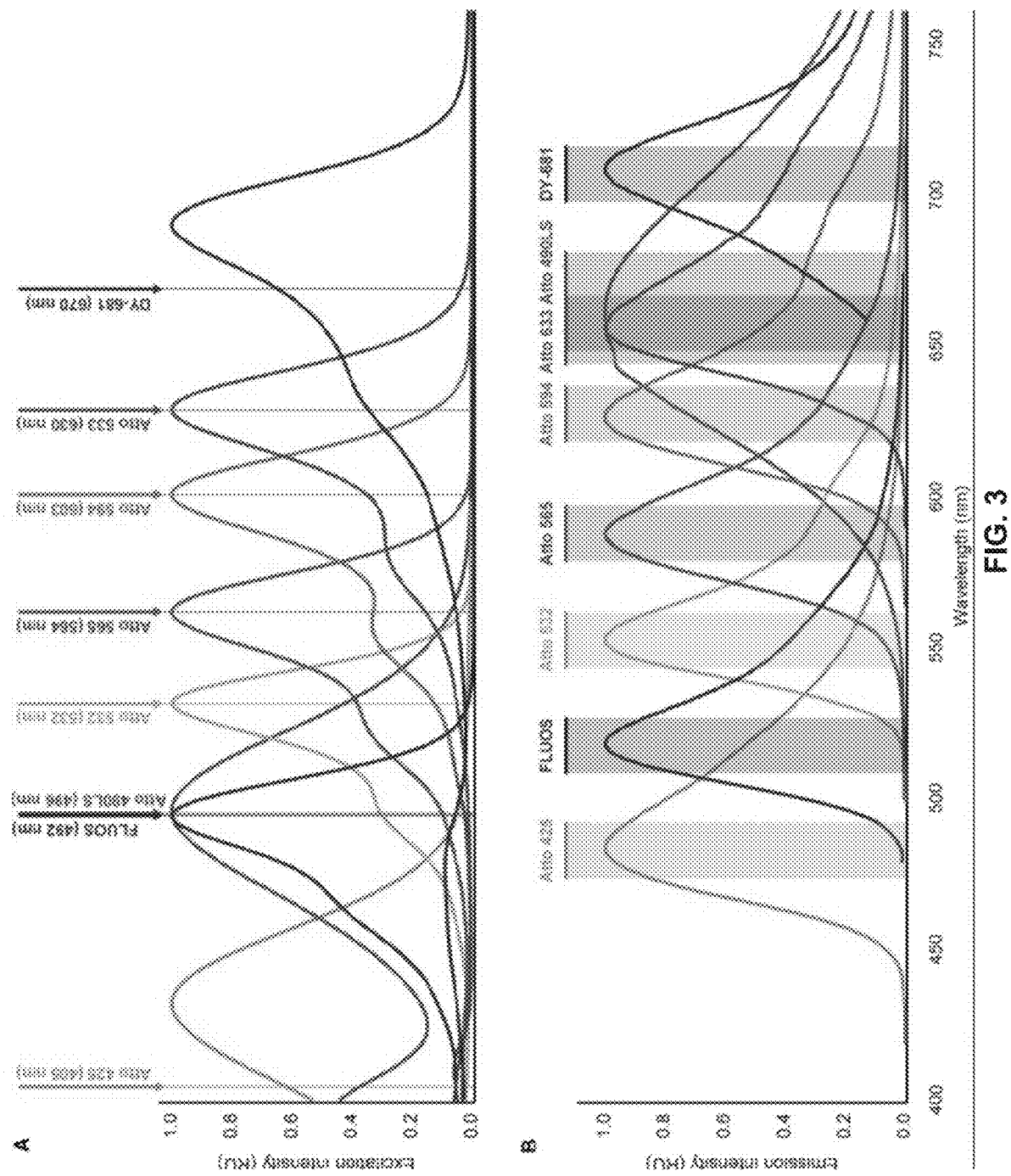
FIG. 3 shows a plots of excitation intensity and emission intensity versus wavelength for example fluorescent probes that can be tagged to Clustered Regularly Interspaced Short Palindromic Repeats (CRISPR) enzymes for each of the two or more target pathogens in the approaches of FIG. 1 and FIG. 2.

FIG. 3 shows a plots of excitation intensity and emission intensity in Raman units (R.U.) versus wavelength in nanometers (nm) for example fluorescent probes that can be tagged to Clustered Regularly Interspaced Short Palindromic Repeats (CRISPR) enzymes for each of the two or more target pathogens in the approach 10. The illustrated example fluorescent probes include Atto 425, FLUOS, Atto 490LS, Atto 532, Atto 565, Atto 594, Atto 633, and DY-681. As can be seen in FIG. 3, excitation intensities for each of the illustrated example fluorescent probes lies within the range of visible wavelengths (i.e., 400 nm to 700 nm). In many embodiments, the multi-wavelength light source 16 is configured to emit light with wavelengths spanning 400 nm to 700 nm so as to effectively excite each of the example fluorescent probes.

As can also be seen in FIG. 3, each of the illustrated example fluorescent probes have a spectrally unique emission intensity profile, which enables the ability to process the signal generated by the multi-wavelength fluorescence detector 18 to identify each of the fluorescent probes activated by detecting the presence of the corresponding spectrally unique emission intensity profile within the signal generated by the multi-wavelength fluorescence detector 18, and thereby detect whether each of the target pathogens is present in the biological sample.

Figure 4:
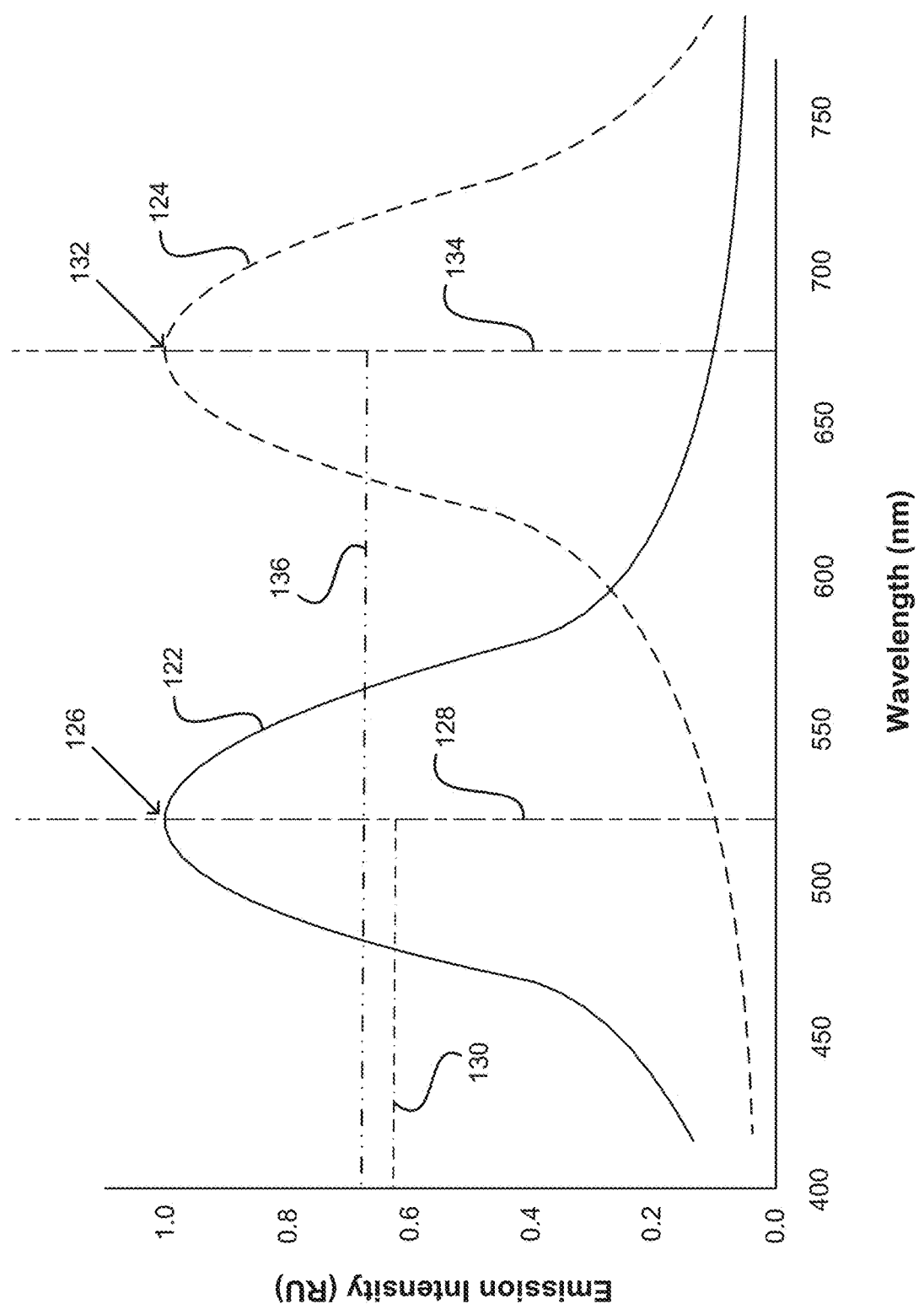
FIG. 4 shows plots of example emission intensity versus wavelength for the presence of each of two different pathogens in a biological sample in the approaches of FIG. 1 and FIG. 2.

FIG. 4 shows plots 122, 124 of example emission intensity versus wavelength for the presence of each of two different pathogens in a biological sample in each of the approaches 10, 100. Plot 122 is a plot of emission intensity versus wavelength indicative of the presence of a first target pathogen in the biological sample for which a first spectrally distinct fluorescent probe (e.g., "FLOUS" as shown in FIG. 3). Plot 124 is a plot of emission intensity versus wavelength indicative of the presence of a second target pathogen in the biological sample for which a second spectrally distinct fluorescent probe (e.g., "Atto 633" as shown in FIG. 3). Any suitable approach can be employed for processing the signal generated by the multi-wavelength fluorescence detector 18 to identify each of the fluorescent probes activated by detecting the presence of the corresponding spectrally unique emission intensity profile within the signal generated by the multi-wavelength fluorescence detector 18. For example, for the first target pathogen, a first measured emission intensity 126 at a first reference wavelength 128 can be compared to a first threshold intensity 130 to determine whether the presence of the first target pathogen is indicated via the first measured emission intensity 126 being greater than the first threshold intensity 130 or the absence of the first target pathogen is indicated via the first measured emission intensity 126 being less than the first threshold intensity 130. Likewise, for the second target pathogen, a second measured emission intensity 132 at a second reference wavelength 134 can be compared to a second threshold intensity 136 to determine whether the presence of the second target pathogen is indicated via the second measured emission intensity 132 being greater than the second threshold intensity 136 or the absence of the second target pathogen is indicated via the second measured emission intensity 132 being less than the second threshold intensity 136.

Figure 5:
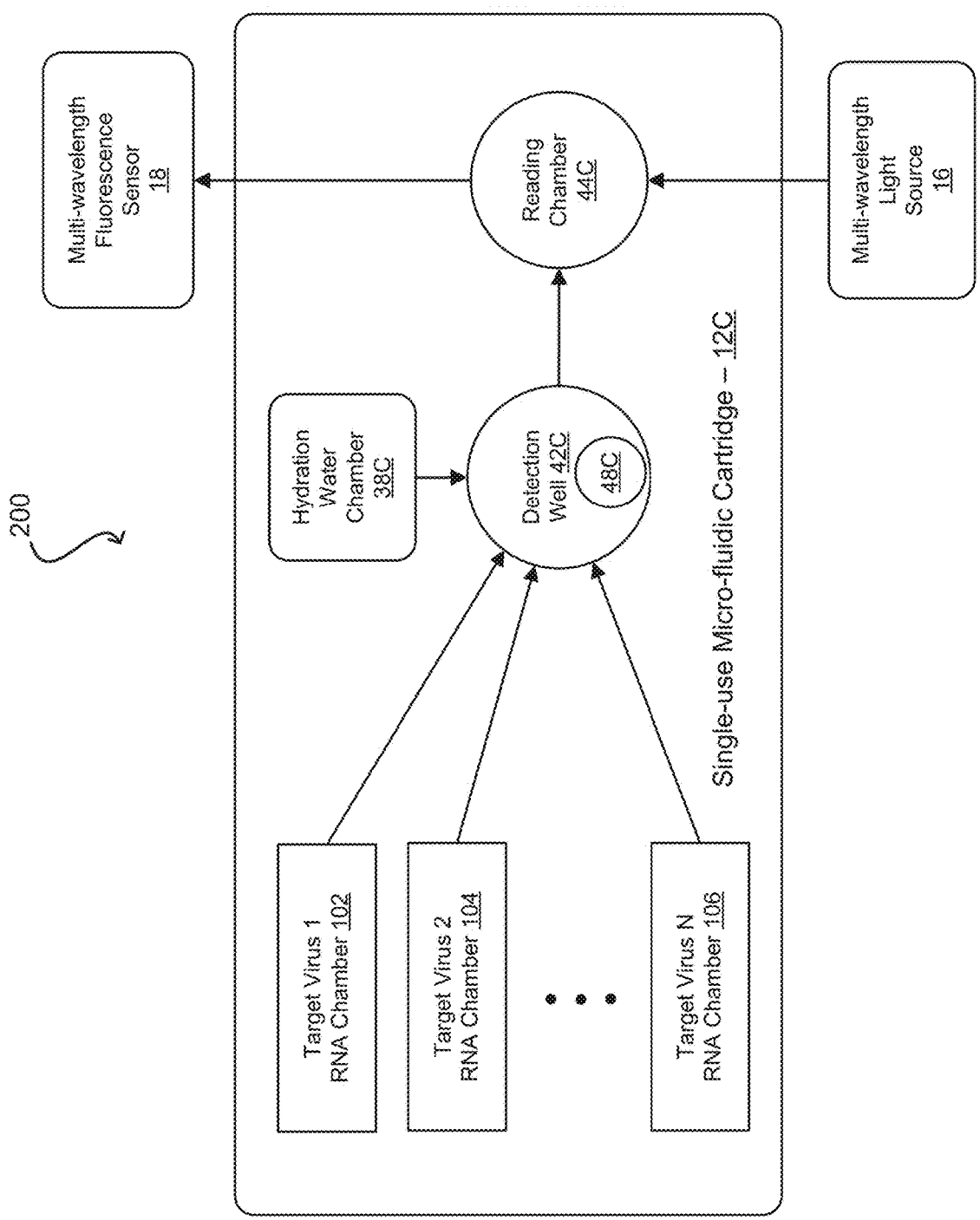
FIG. 5 shows a simplified schematic diagram of an approach for generating a multi-wavelength signal indicative of the presence of a target pathogen that can be employed in the approaches of FIG. 1 and FIG. 2.

FIG. 5 shows a simplified schematic diagram of an approach 200 that can be employed in the approach 10 for generating a spectral signal indicative of the presence of any suitable combination of target pathogens, including any 1, 2, 3, 4, or more target pathogens. The processing of the signal generated by the multi-wavelength fluorescence detector 18 in the approach 10 can include comparison with the spectral signal(s) generated in the approach 200 to determine whether each of the target pathogens are present in the biological sample.

Figure 6:
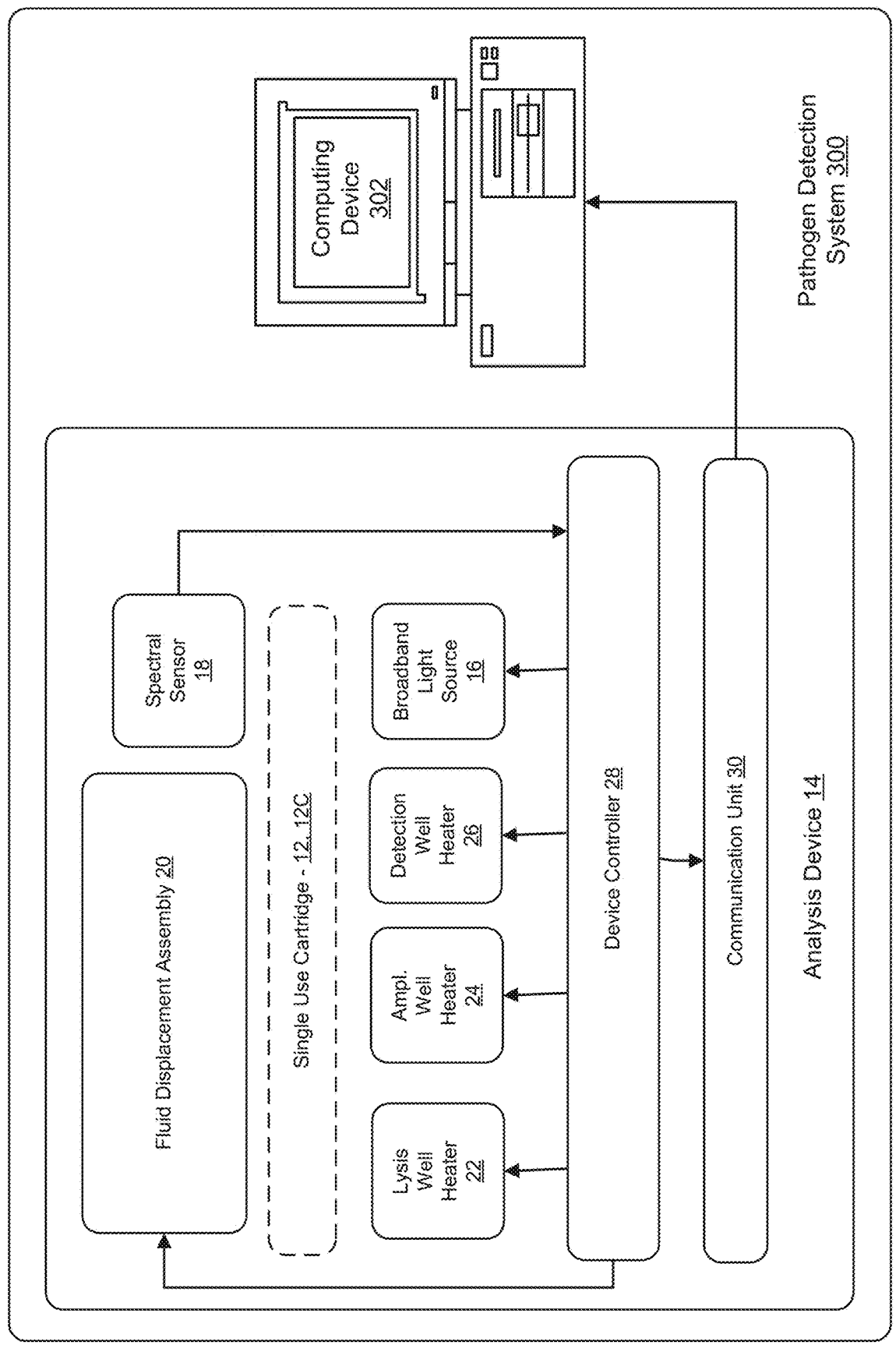
FIG. 6 is a simplified schematic diagram of a system for testing a biological sample for each of two or more target pathogens, in accordance with the approaches of FIG. 1 and FIG. 2.

In the illustrated embodiment, the approach 200 is implemented using a single-use microfluidic cartridge 12C and the analysis device 14 (shown in FIG. 6). The cartridge 12C includes one or more target pathogen RNA chambers 102, 104, 106, a hydration water chamber 38C, an amplification well 40C, a detection well 42C, and a reading chamber 44C. Each of the one or more target pathogen RNA chambers 102, 104, 106 store RNA of a respective target pathogen. The device controller 28 controls operation of the fluid displacement assembly 20 to transfer of target pathogen RNA from each of the one or more target pathogen RNA chambers 102, 104, 106 and hydration water from the hydration water chamber 38C to the amplification well 40C, which contains the above-described amplification compounds 46 for each of the one or more target pathogens. The device controller 28 controls operation of the amplification well heater 24 to heat the resulting liquid in the amplification well 40C to produce RT-LAMP of each of the one or more target pathogens. The device controller 28 controls operation of the fluid displacement assembly 20 to transfer liquid from the amplification well 40C to the detection well 42C. In many embodiments, the detection well 42 includes the above-described detection cycle compounds 48 for each of the one or more target pathogens. The device controller 28 controls operation of the detection well heater 26 to control the temperature of the resulting liquid in the detection well 42C. The device controller 28 controls operation of the fluid displacement assembly 20 to transfer liquid from the detection well 42C to the reading chamber 44C.

The device controller 28 controls operation of the multi-wavelength light source 16 to emit multi-wavelength excitation light (e.g., white light) onto the liquid in the reading chamber 44C. The multi-wavelength excitation light causes the liquid in the reading chamber 44 to emit a fluorescent light corresponding to the spectrally specific fluorescent probes employed and which of the one or more target pathogens that is/are present. The multi-wavelength fluorescence detector 18 generates a control fluorescence light detection signal in response to the fluorescence light emitted by the liquid in the reading chamber 44C.

FIG. 6 is a simplified schematic diagram of a system 300 for testing a biological sample for each of two or more target pathogens, in accordance with the approach 10. The system 300 includes the single-use microfluidic cartridge 12, the analysis device 14, and a computing device 302. In many embodiments, the analysis device 14 operates the cartridge 12 as described herein and generates, via the multi-wavelength fluorescence detector 18, an output signal that is communicated to the computing device 302 via the communication unit 30. In such embodiments, the computing device 302 process the signal generated by the multi-wavelength fluorescence detector 18 to identify each of the fluorescent probes activated by detecting the presence of the corresponding spectrally unique emission intensity profile within the signal generated by the multi-wavelength fluorescence detector 18, and thereby detect whether each of the target pathogens is present in the biological sample.

Figure 7:
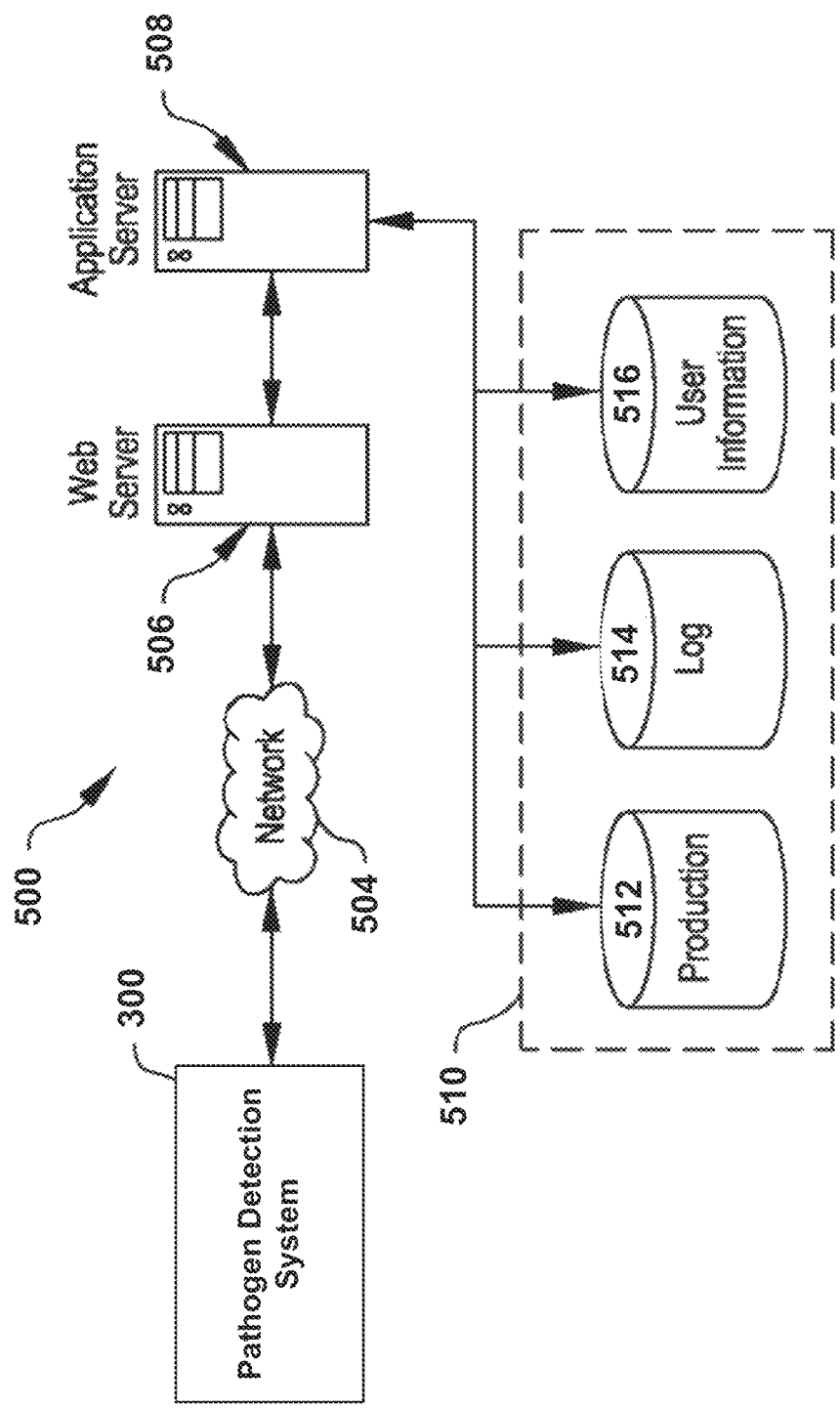
FIG. 7 illustrates an environment in which various embodiments can be implemented.

FIG. 7 illustrates aspects of an example environment 500 for implementing aspects in accordance with various embodiments. As will be appreciated, although a Web-based environment is used for purposes of explanation, different environments may be used, as appropriate, to implement various embodiments. The environment includes the pathogen detection system 300, which can include any appropriate device operable to send and receive requests, messages, or information over an appropriate network 504 and convey information back to a user of the device. Examples of such client devices include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 506 for receiving requests and serving content in response thereto, although for other networks an alternative device serving a similar purpose could be used as would be apparent to one of ordinary skill in the art.

The illustrative environment includes at least one application server 508 and a data store 510. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the system 10 and the application server 508, can be handled by the Web server. It should be understood that the Web and application servers are not required and are merely example components, as structured code discussed herein can be executed on any appropriate device or host machine as discussed elsewhere herein.

The data store 510 can include several separate data tables, databases or other data storage mechanisms and media for storing data relating to a particular aspect. For example, the data store illustrated includes mechanisms for storing production data 512 and user information 516, which can be used to serve content for the production side. The data store also is shown to include a mechanism for storing log data 514, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 510. The data store 510 is operable, through logic associated therewith, to receive instructions from the application server 508 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the electronic device 16. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 7. Thus, the depiction of the system 500 in FIG. 7 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGI") servers, data servers, Java servers, and business application servers. The server(s) also may be capable of executing programs or scripts in response to requests from user devices, such as by executing one or more Web applications that may be implemented as one or more scripts or programs written in any programming language, such as Java®, C, C#, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for testing a biological sample for each of two or more target pathogens, the system comprising:
    a cartridge comprising a detection cycle well and a fluorescence reading chamber, wherein the cartridge is configured to receive a biological sample, wherein the detection cycle well comprises respective Clustered Regularly Interspaced Short Palindromic Repeats (CRISPR) enzymes for each of the two or more target pathogens, and wherein the respective CRISPR enzymes are tagged with respective spectrally unique fluorescent probes;
    an analysis device comprising a broadband light source and a spectral sensor configured to detect light wavelengths comprising a respective light wavelength corresponding to each of the spectrally unique fluorescent probes; and
    at least one controller configured to:
        control operation of the cartridge to combine a portion of the biological sample with the CRISPR enzymes to form a detection cycle liquid within the detection cycle well;
        control operation of the cartridge to transfer a portion of the detection cycle liquid from the detection cycle well to the fluorescence reading chamber;
        control operation of the broadband light source to emit a broadband fluorescence excitation light onto the detection cycle liquid in the fluorescence reading chamber;
        receive a fluorescence light emission detection signal generated by the spectral sensor in response to a fluorescence light emitted by the detection cycle liquid in the fluorescence reading chamber; and
        process the fluorescence light emission detection signal to generate detection data indicative of presence or absence of each of the two or more target pathogens in the biological sample.

2. The system of claim 1, wherein the spectral sensor is configured to detect the fluorescence light emitted by the detection cycle liquid in a wavelength band comprising 350 nm to 1000 nm.

3. The system of claim 1, wherein:
    the cartridge further comprises an amplification cycle well comprising loop-mediated isothermal amplification (LAMP) primers for reverse transcription loop-mediated isothermal amplification (RT-LAMP) of each of the two or more target pathogens, and
    the at least one controller is further configured to:
        control operation of the cartridge to perform RT-LAMP on a portion of the biological sample disposed within the amplification cycle well to form an amplified sample liquid; and
        control operation of the cartridge to transfer a portion of the amplified sample liquid to the detection cycle well.

4. The system of claim 1, wherein the two or more target pathogens comprise at least one of SARS-COV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V.

5. A system for testing a biological sample for each of two or more target pathogens, the system comprising:
    a detection cycle well comprising respective Clustered Regularly Interspaced Short Palindromic Repeats (CRISPR) enzymes for each of the two or more target pathogens, and wherein the respective CRISPR enzymes are tagged with respective spectrally unique fluorescent probes;
    a multi-wavelength light source;
    a spectral sensor configured to detect light wavelengths comprising a respective light wavelength corresponding to each of the spectrally unique fluorescent probes; and
    at least one controller configured to:
        control operation of the multi-wavelength light source to emit multi-wavelength fluorescence excitation light onto a detection cycle liquid formed within the detection cycle well via combination of a biological sample with the CRISPR enzymes;
        receive a fluorescence light emission detection signal generated by the spectral sensor in response to a fluorescence light emitted by the detection cycle liquid; and
        process the fluorescence light emission detection signal to generate detection data indicative of presence or absence of each of the two or more target pathogens in the biological sample.

6. The system of claim 5, further comprising:
a control detection cycle well comprising respective control CRISPR enzymes for each of the two or more target pathogens, and wherein the respective control CRISPR enzymes are tagged with respective spectrally unique fluorescent probes;
one or more light sources comprising the multi-wavelength light source;
one or more spectral sensors comprising the spectral sensor, wherein each of the one or more spectral sensors is configured to detect light wavelengths comprising respective light wavelengths corresponding to each of the spectrally unique fluorescent probes; and
the at least one controller is further configured to:
control operation of the one or more light sources to emit a control multi-wavelength fluorescence excitation light onto a control detection cycle liquid formed within the control detection cycle well via combination of a sample of at least a portion of each of the two or more target pathogens with the control CRISPR enzymes;
receive a control fluorescence light emission detection signal generated by the one or more spectral sensors in response to a control fluorescence light emitted by the control detection cycle liquid; and
process the control fluorescence light emission detection signal to determine at least one of: whether the detection data is valid or whether the detection data is invalid.

7. The system of claim 5, wherein the spectral sensor is configured to detect the fluorescence light emitted by the detection cycle liquid in a wavelength band from 350 nm to 1000 nm.

8. The system of claim 5, wherein the two or more target pathogens comprise at least one of SARS-COV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V.

9. The system of claim 5, wherein the detection data is indicative of intensity of the fluorescence light emitted by the detection cycle liquid at predetermined wavelengths comprising a unique wavelength for each of the two or more target pathogens.

10. The system of claim 5, further comprising:
a single-use microfluidic cartridge comprising the detection cycle well; and
an analysis device comprising the multi-wavelength light source and the spectral sensor.

11. The system of claim 10, wherein:
the single-use microfluidic cartridge further comprises a sample swab chamber and an amplification cycle well, wherein the sample swab chamber is configured to receive at least a portion of a swab comprising the biological sample, wherein the amplification cycle well comprises loop-mediated isothermal amplification (LAMP) primers for reverse transcription loop-mediated isothermal amplification (RT-LAMP) of each of the two or more target pathogens; and
the at least one controller is further configured to:
control operation of the single-use microfluidic cartridge to transfer a portion of the biological sample from the sample swab chamber to the amplification cycle well;
control operation of the single-use microfluidic cartridge to perform RT-LAMP amplification on the portion of the biological sample disposed within the amplification cycle well to form an amplified sample liquid; and
control operation of the single-use microfluidic cartridge to transfer a portion of the amplified sample liquid to the detection cycle well to combine with the CRISPR enzymes to form the detection cycle liquid.

12. A method of testing a biological sample for each of two or more target pathogens, the method comprising:
forming a detection cycle liquid by combining detection cycle compounds with a biological sample liquid formed from a biological sample, wherein the detection cycle compounds comprise respective Clustered Regularly Interspaced Short Palindromic Repeats (CRISPR) enzymes for each of the two or more target pathogens, and wherein the respective CRISPR enzymes are tagged with respective spectrally unique fluorescent probes;
exposing the detection cycle liquid to a multi-wavelength fluorescence excitation light;
generating a fluorescence light emission detection signal indicative of intensity of fluorescence light emitted by the detection cycle liquid at two or more wavelengths; and
processing the fluorescence light emission detection signal to generate detection data indicative of presence or absence of each of the two or more target pathogens in the biological sample.

13. The method of claim 12, further comprising forming the biological sample liquid by performing reverse transcription loop-mediated isothermal amplification (RT-LAMP) of the biological sample, wherein the biological sample is combined with loop-mediated isothermal amplification (LAMP) primers.

14. The method of claim 12, further comprising:
emitting a control multi-wavelength fluorescence excitation light onto a control detection cycle liquid formed within a control detection cycle well via combination of a sample of at least a portion of each of the two or more target pathogens with control CRISPR enzymes for each of the two or more target pathogens, and wherein the respective control CRISPR enzymes are tagged with respective spectrally unique fluorescent probes;
receiving a control fluorescence light emission detection signal generated in response to a control fluorescence light emitted by the control detection cycle liquid; and
processing the control fluorescence light emission detection signal to determine at least one of: whether the detection data is valid or whether the detection data is invalid.

15. The method of claim 14, further comprising performing RT-LAMP amplification on an unamplified sample of at least a portion of each of the two or more target pathogens to form the sample of at least a portion of each of the two or more target pathogens.

16. The method of claim 12, wherein the two or more target pathogens comprise at least one of SARS-COV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V.

17. The method of claim 12, wherein the fluorescence light emission detection signal is indicative of intensity of fluorescence light emitted by the detection cycle liquid over a range of wavelengths comprising 400 nm to 800 nm.

18. The method of claim 12, wherein the fluorescence light emission detection signal is generated by a spectral sensor.

19. The method of claim 12, further comprising generating, for each of the two or more target pathogens, training data indicative of presence the target pathogen in a biological sample, wherein the training data is employed in the processing of the fluorescence light emission detection signal to generate the detection data.

20. The method of claim 12, wherein an analysis device operates a single-use microfluidic cartridge to form the detection cycle liquid, expose the detection cycle liquid to the multi-wavelength fluorescence excitation light, and generate the fluorescence light emission detection signal.

* * * * *